United States Patent [19]

Migliori

[11] Patent Number: 5,062,296

[45] Date of Patent: Nov. 5, 1991

[54] RESONANT ULTRASOUND SPECTROSCOPY

[75] Inventor: Albert Migliori, Santa Fe, N. Mex.

[73] Assignee: The United States of America as represented by the Department of Energy, Washington, D.C.

[21] Appl. No.: 585,557

[22] Filed: Sep. 20, 1990

[51] Int. Cl.$^5$ ............................................. G01N 29/12
[52] U.S. Cl. ........................................... 73/579; 73/659
[58] Field of Search ................. 73/579, 597, 602, 659, 73/664

[56] References Cited

U.S. PATENT DOCUMENTS

| | | | |
|---|---|---|---|
| 2,393,225 | 1/1946 | Andalikiewicz | 73/579 |
| 2,909,059 | 10/1959 | Laue | 73/579 |
| 3,043,132 | 7/1962 | Schubring | 73/579 |
| 3,948,345 | 4/1976 | Rosencwaig | 73/659 |
| 4,285,241 | 8/1981 | Smith et al. | 73/579 |
| 4,428,235 | 1/1984 | Sugiyama | 73/579 |
| 4,581,395 | 4/1986 | Breazeale | 73/602 |
| 4,704,905 | 11/1987 | Arora | 73/602 |
| 4,758,964 | 7/1988 | Bittner et al. | 364/508 |
| 4,829,823 | 5/1989 | Michel | 73/579 |

OTHER PUBLICATIONS

"Spectrum Analysis: A New Tool for Quality Control by Ultrasonics", Canella, G. & Monti, F. (Not International Aug. 1976, vol. 9, No.4).

Primary Examiner—Hezron E. Williams
Assistant Examiner—Rose M. Finley
Attorney, Agent, or Firm—Ray G. Wilson; Paul D. Gaetjens; William R. Moser

[57] ABSTRACT

A resonant ultrasound spectroscopy method provides a unique characterization of an object for use in distinguishing similar objects having physical differences greater than a predetermined tolerance. A resonant response spectrum is obtained for a reference object by placing excitation and detection transducers at any accessible location on the object. The spectrum is analyzed to determine the number of resonant response peaks in a predetermined frequency interval. The distribution of the resonance frequencies is then characterized in a manner effective to form a unique signature of the object. In one characterization, a small frequency interval is defined and stepped though the spectrum frequency range. Subsequent objects are similarly characterized where the characterizations serve as signatures effective to distinguish objects that differ from the reference object by more than the predetermined tolerance.

6 Claims, 9 Drawing Sheets

RESONANT ULTRASOUND SPECTROSCOPY

BACKGROUND OF INVENTION

The present invention relates to ultrasonics and, more particularly, to the ultrasonic resonant response of components. This invention is the result of a contract with the Department of Energy (Contract No. W-7405-ENG-36).

Ultrasonics has a number of applications to the determination of various material and component characteristics. In one application, the transmission of ultrasonic waves is detected to determine the presence of internal anomalies in a component. In another application, the thickness of a component is determined from the resonant response of a portion of the component located adjacent a transmitter/receiver transducer. These applications generally require transducer access to a flat surface in proximity to a localized volume of the component to be measured. Yet another application involves modal analysis, where the acoustic resonances of a component are excited and the response amplitudes are measured to predict component failure. All these applications depend on the amplitude of a detected response, which, in turn, may depend on the temperature, the exact location of the transducer, acoustic coupling, and other variables.

Resonant ultrasound spectroscopy has been used to determine various properties of solid materials, particularly elastic constants. This application is discussed in U.S. patent application Ser. No. 406,007, now U.S. Pat. No. 4,967,148 Resonant Ultrasound Spectrometer, incorporated herein by reference. The resonant response spectrum of small parallelepiped specimens is determined for use in computing the material elastic constants.

It would be desirable to provide an ultrasonic inspection method that does not require flat surfaces for application of the acoustic wave, that provides reproducible results independent of the location of the transmitter/receive transducers, and is relatively insensitive to temperature, coupling, and other variables that are difficult to control. These problems are addressed by the present invention and a resonant ultrasound spectrographic technique is presented for uniquely characterizing an object.

Accordingly, it is an object of the present invention to provide a characteristic ultrasonic signature of an object that is not dependent on a particular location of ultrasonic transducers.

It is another object of the present invention to provide an ultrasonic inspection method that does not require flat surfaces for the introduction and reception of an acoustic wave.

One other object is to provide an acoustic signature that is relatively insensitive to uncontrolled variables such as temperature and acoustic coupling.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF INVENTION

To achieve the foregoing and other objects, and in accordance with the purposes of the present invention, as embodied and broadly described herein, the method of this invention may comprise characterizing an object by resonant ultrasound spectroscopy. Acoustic waves are applied to an object and swept over a predetermined frequency range. The resonant spectrum of the object is determined over the predetermined frequency range. The frequency distribution of the resonance response peaks over the frequency range is then characterized to form a unique signature to structurally identify the object.

In one technique, a series of relatively small response intervals are defined within the entire frequency range and the number of resonant response peaks within each interval is determined. The density of the resonant response peaks in each small interval is then determined to form the unique characterization of the object. Other characterizations may utilize a conventional Gaussian curve for weighting the response peak density over the entire frequency range and a simple histogram with windows uniformly distributed over the frequency range.

BRIEF DESCRIPTION OF THE DRAWINGS

The accompanying drawings, which are incorporated in and form a part of the specification, illustrate the present invention and, together with the description, serve to explain the principles of the invention. In the drawings.

DETAILED DESCRIPTION OF THE INVENTION

Every object, by virtue of its shape, size and physical properties (e.g., elastic moduli, speed of sound, density, etc.) can be made to resonate, i.e., vibrate resonantly, at a multitude of frequencies if its ultrasonic attenuation is low enough. The number of observable resonant frequencies depends upon the geometrical complexity of the object, its ultrasonic attenuation, and the various modes of vibration possible, e.g., bulk mode, shear mode, torsional mode, etc. Even an object as simple as a metal cube has a large number of observable resonant frequencies. A complex object may possess thousands of resonant frequencies ranging from a few thousand hertz to a few megahertz, for typical objects that might be tested.

These resonant frequencies provide an acoustic signature of a given object that can be formed into a unique characterization of the object and is not dependent on amplitude of the response or subject to the many variables that affect the amplitude. A resolution can be selected to enable the characterization to serve as a signature for object selection or a quality control measure. The signature serves to compare two objects, including their internal compositions, within selected tolerance levels, thereby enabling the presence of small differences or flaws to be detected, even though not spatially located.

Figure 1:
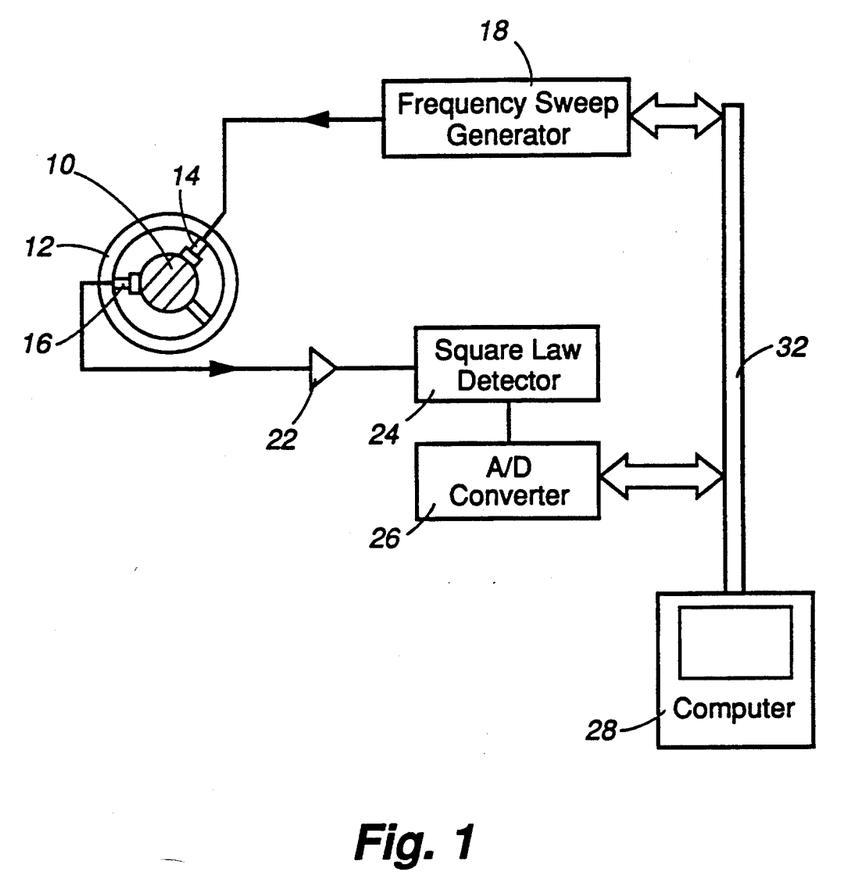
FIG. 1 is a schematic diagram in block diagram form of apparatus for performing resonant ultrasound spectroscopy.

Referring now to FIG. 1, there is shown a resonant ultrasound spectrometry system according to the present invention. A test object 10 is located within a transducer assembly 12 with a transmit transducer 14 and a receive transducer 16 contacting object 10. In accordance with the present invention, the locations of transducers 14 and 16 on object 10 are not critical, although transducers 14 and 16 should be similarly located on similar objects in order to provide best comparative results. The locating surfaces on object 10 are not required to be flat and only a mechanical point contact is adequate for the present technique. Likewise, there is no requirement to optimize acoustic coupling between a transducer and a surface of object 10.

Frequency sweep generator 18 outputs a signal to transmit transducer 14 that is effective for exciting object 10 with acoustic waves having a frequency that is swept over a predetermined frequency range. The frequency range is preferably selected to yield resonant responses that are independent of the environment, e.g. the mounting structure supporting object 10, ground vibrations, etc., and to contain a large number of resonances from object 10. The size and physical features of object 10 determine the frequency range and the required accuracy for the measurements. Typically, if the physical difference between a reference object and an object under test is at least 1%, the difference should be detectable. Also, considering that the speed of sound in solids is typically within a factor of two of 4 kM/s, a 1 mm feature would require megahertz frequencies, while a 1 meter feature would require frequencies near 1 kHz. The response of object 10 is detected by transducer 16, amplified by amplifier 22 and provided to detector 24. A suitable detector is described in U.S. patent application Ser. No. 406,007, referenced above, although many other detectors are available. The response is converted to digital form by A/D converter 26 for further processing.

Computer 28 communicates with frequency sweep generator 18 and A/D converter 26 along bus 32, an IEEE 488 bus. Computer 28 controls the sweep rate of generator 18 and receives frequency data to correlate with response data from A/D converter 26. Computer 28 further performs the resonant peak analysis according to the present invention to form a unique characterization of object 10 with a selected sensitivity. Any of a number of available software routines may be used to identify the frequencies of the resonance peaks.

The object characterization of the present invention is formed by first determining the frequency of each resonant response peak along the entire frequency range of interest. The distribution of the resonant response frequencies is then characterized to form a unique acoustic signature for the object. In one method of forming the signature, a relatively small response interval is defined for stepping over the overall frequency range. The number of resonant response peaks is then determined over each of the relatively small response intervals. The number of resonant peaks in the small interval at each step is plotted as a function of frequency to form one unique object characterization.

Define a function $F_i$ such that $F_i = 0$ at frequency $f_i$ for no resonance;

$F_i = 1$ at frequency $f_i$ if a resonance is present, where $f_1 \leq f_i \leq f_N$, the frequency range over which the resonant frequencies were determined along N data points. The signature plot for a stepped interval signature is then $$S_i^1 = \sum_{l=i}^{l=i+k} F_l,$$

where k is the step interval width.

Other distributions of the resonant frequencies may be selected to form a unique characterization with different sensitivities to differences between components. A Gaussian function may be used over the entire interval as a weighting function that slides across the resonance spectrum. The Gaussian signature plot becomes $$S_i^2 = \sum_{j=1}^{N} F_j e^{\frac{-(f_i - f_j)^2}{\Delta f}},$$

where $\Delta f$ is a selected window width. Likewise, a simple histogram may be formed, with a histogram signature plot formed as $$S_i^3 = \sum_{(i-1)M+1}^{iM} F_j,$$

where M is the window width and i runs from 1 to the number of windows. It will be appreciated that the subject characterizations are a function only of the frequency and not the amplitude of the resonant response peaks.

By way of example, assume an appropriate frequency range is chosen from 200 kHz to 400 kHz and the sweep generator is stepped at intervals of 100 Hz over this range. The response of the object is recorded at each step to generate a resonant response spectrum. This total response is then reduced to a characterization that is relatively insensitive to uncontrolled variables, such as temperature, and that has a variable selectivity determined by the width selected for the small response interval.

Figure 2A:
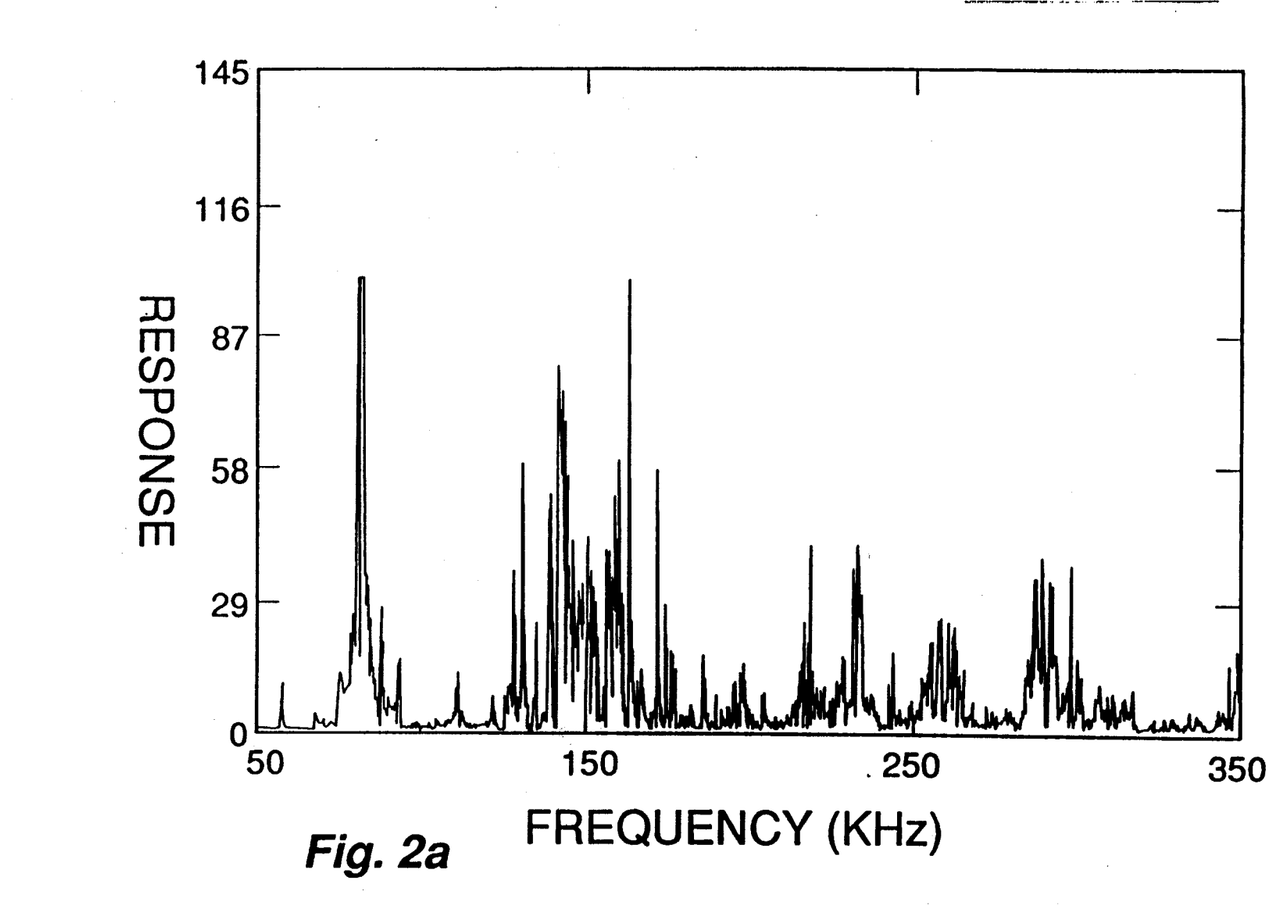
FIG. 2A graphically depicts a resonance spectrum from a first object.

For a stepped interval characterization, a relatively small response interval is selected, e.g., 2000 Hz, and is incremented along the entire frequency range in steps corresponding to the sweep steps. The number of resonant response peaks is then calculated within the small response interval at each step. In this example, one counting interval would be between 200 kHz and 202 kHz, another interval between 200.1 kHz and 202.1 kHz, etc. A total of 1980 peak densities would be obtained corresponding to each of the interval steps. The distribution of resonant peak densities as a function of frequency then forms the unique object signature according to the present invention. FIGS. 2A, 2B, 2C, 2D, 3A, 3B, 3C, and 3D illustrate the characterizations discussed above and demonstrate the ability to differentiate an object containing a difference from a reference object. In each case, a basic brass plate was provided with dimensions of 5×10 cm and 1.5 mm thickness and an edge slot 1 mm wide×4 mm deep. The only distinction was that the edge slots were at locations that differed by 2 mm. FIGS. 2A and 3A are the resonant response spectra for the two different pieces.

Figure 2B:
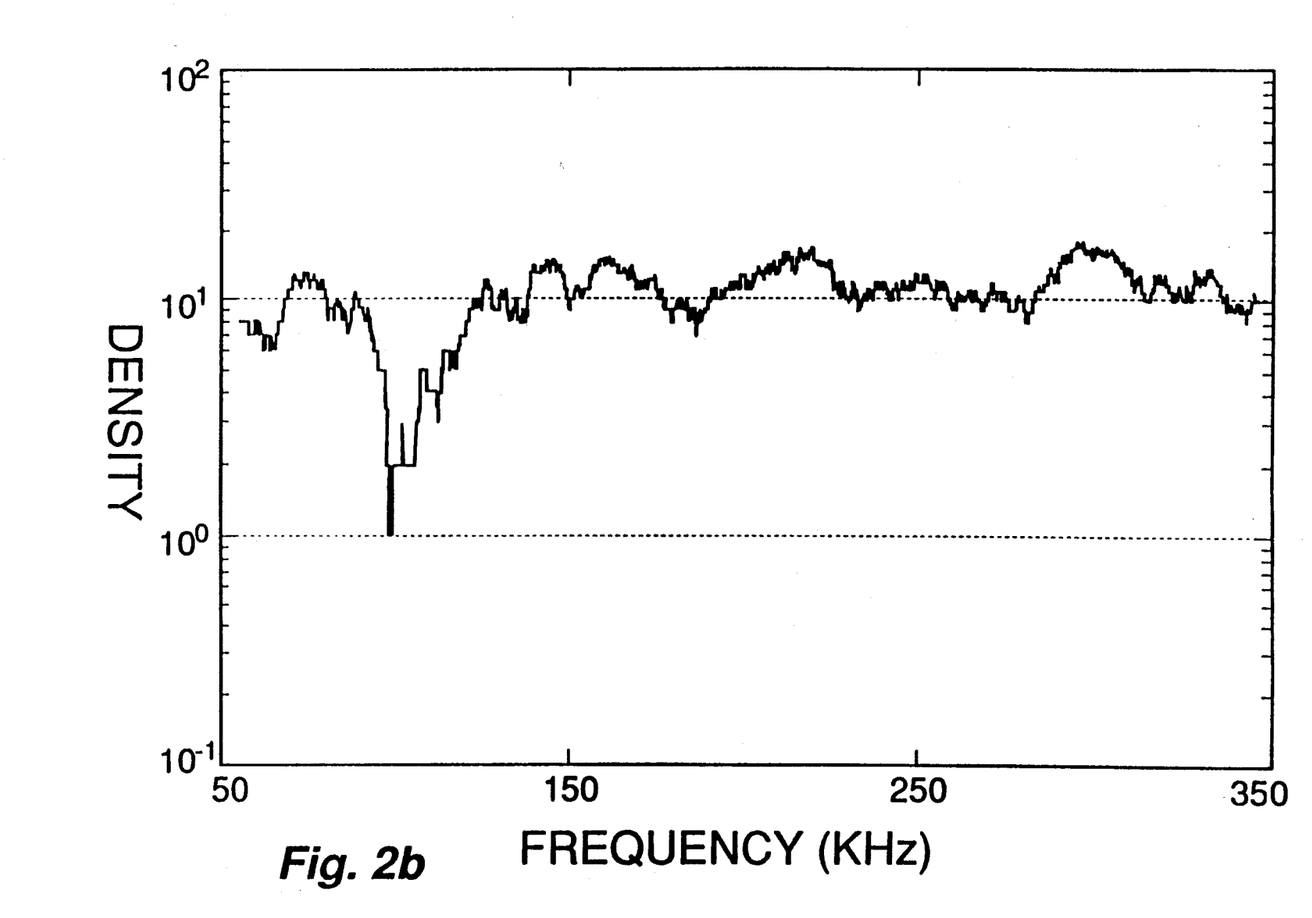
FIG. 2B graphically depicts a stepped interval resonance characterization of the first object calculated from the resonance response shown in FIG. 2A.
Figure 3A:
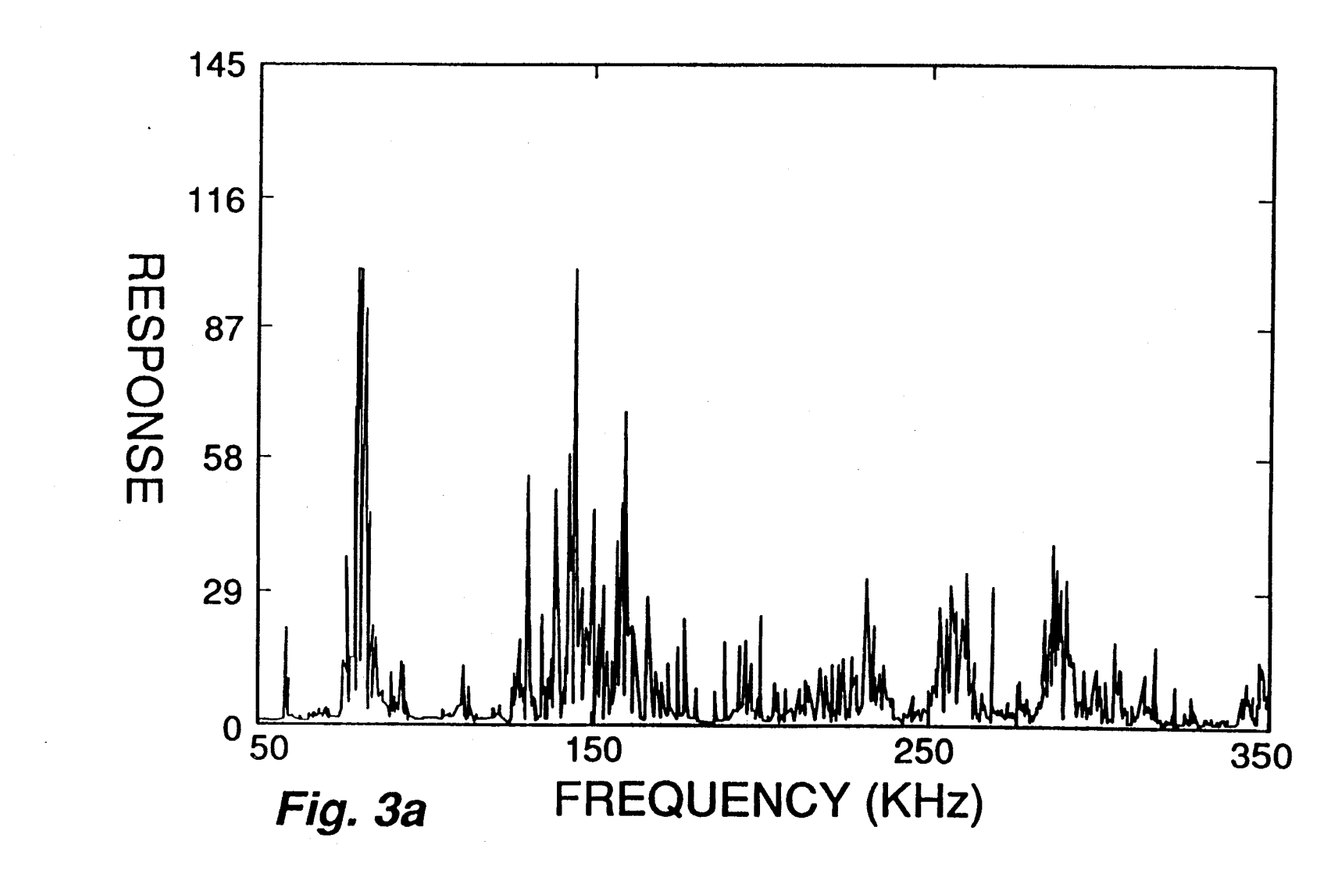
FIG. 3A graphically depicts a resonance spectrum from a second object.
Figure 3B:
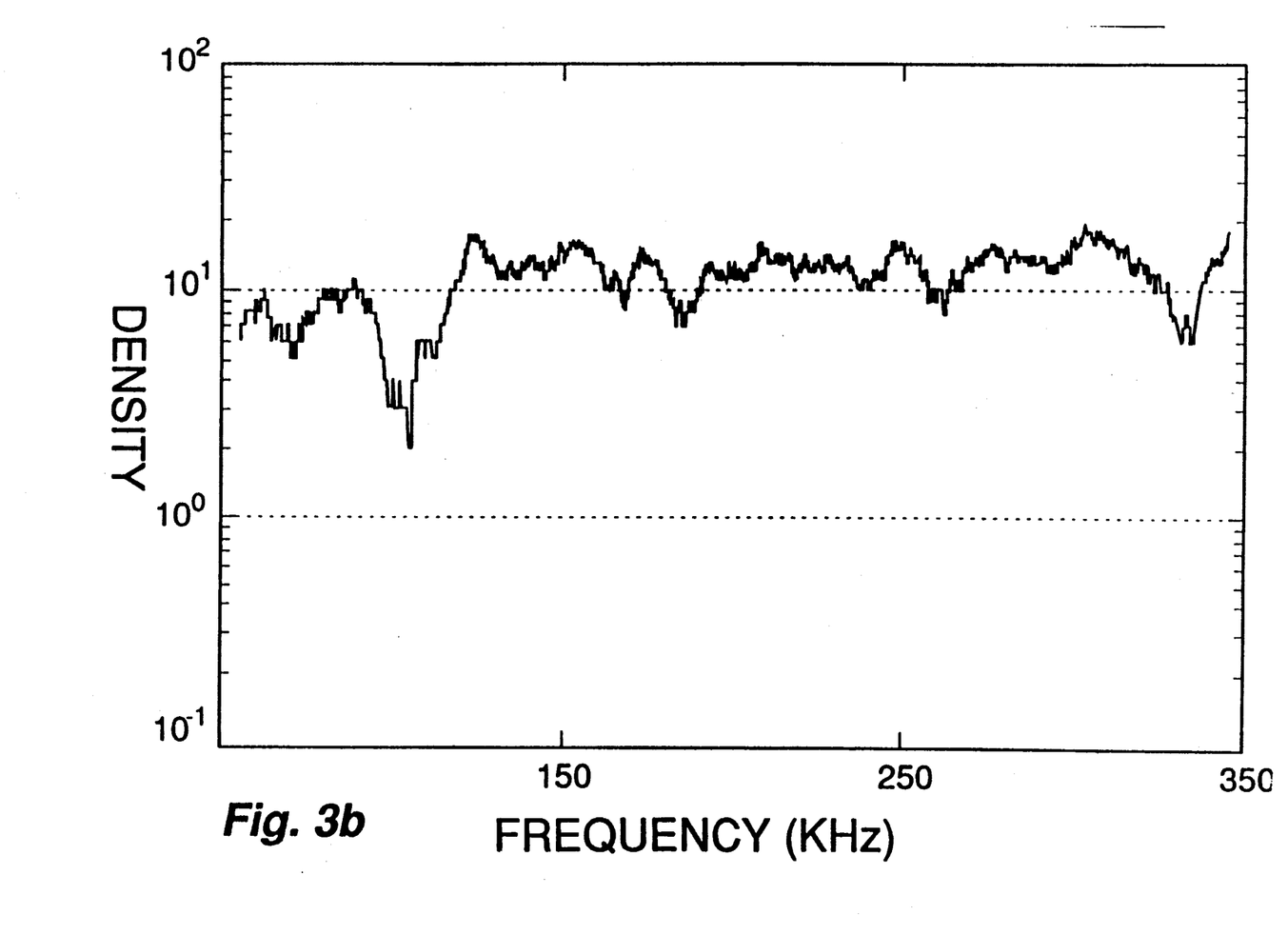
FIG. 3B graphically depicts a stepped interval resonance characterization of the second object calculated from the resonance response shown in FIG. 3B.

FIGS. 2B and 3B are the corresponding stepped interval characteristic resonance density plots. The entire frequency range of 350 kHz was swept by the exciting signal to generate the resonant spectra shown in FIGS. 2A and 3A. A second interval of 2 kHz was then stepped through the entire frequency range in 0.1 kHz steps to obtain the numbers of resonant response peaks in each second interval. These numbers of resonant response peaks form a unique characterization of the object and can be formulated as a density (number of peaks/step) or a percentage relative to the resonant peaks in the entire sweep frequency range. The distinction between the two characteristic curves 2B and 3B is readily apparent and, in this example, can be recognized manually or through a computer comparison scheme.

The selectivity of the above characterization can be varied by adjusting the width of the small response interval and the length of the step through the total frequency range. It is readily apparent that the response interval and step length control the density distribution characterization to enhance or obscure the effect of various resonance peak distributions.

Figure 2C:
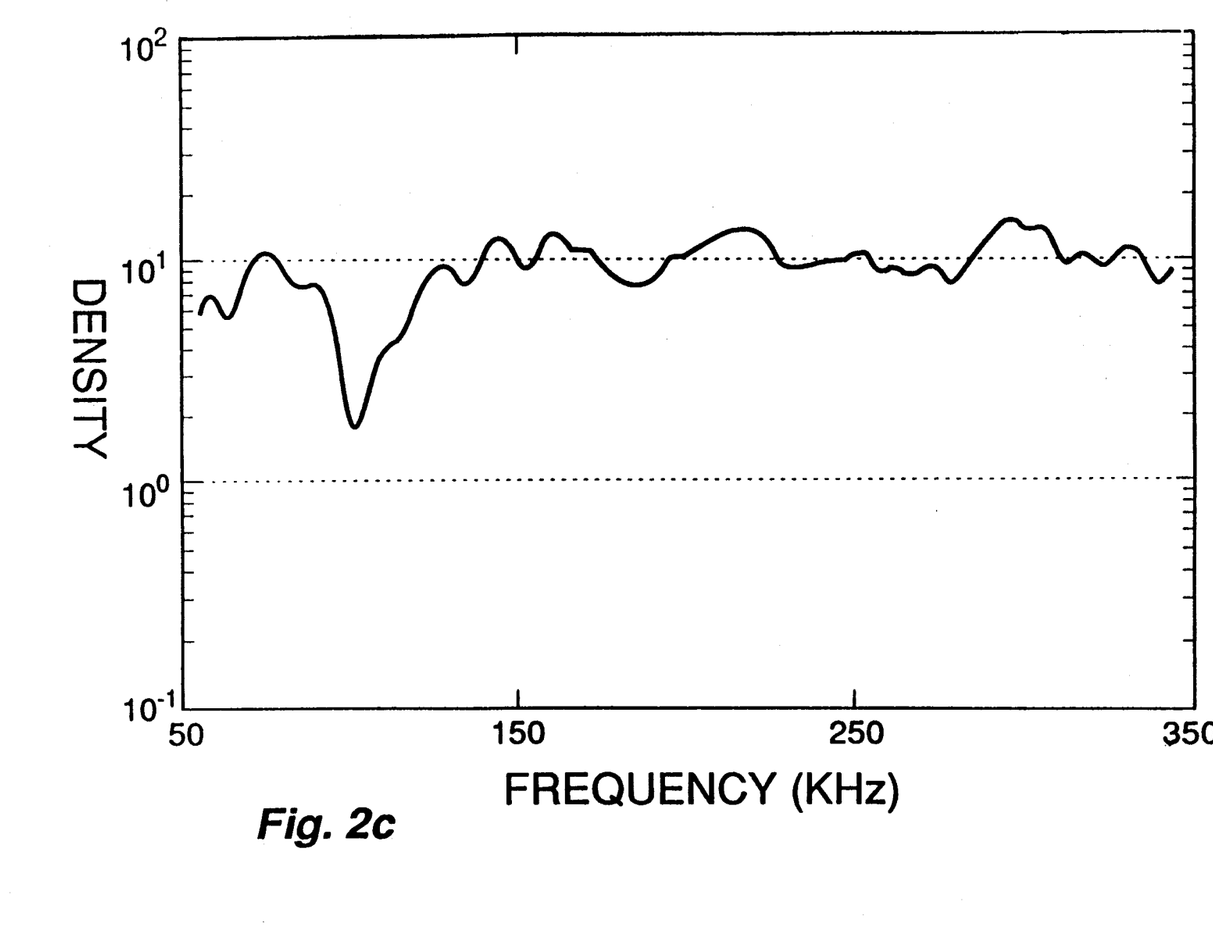
FIG. 2C graphically depicts a Gaussian characterization calculated from the resonance response shown in FIG. 2A.
Figure 2D:
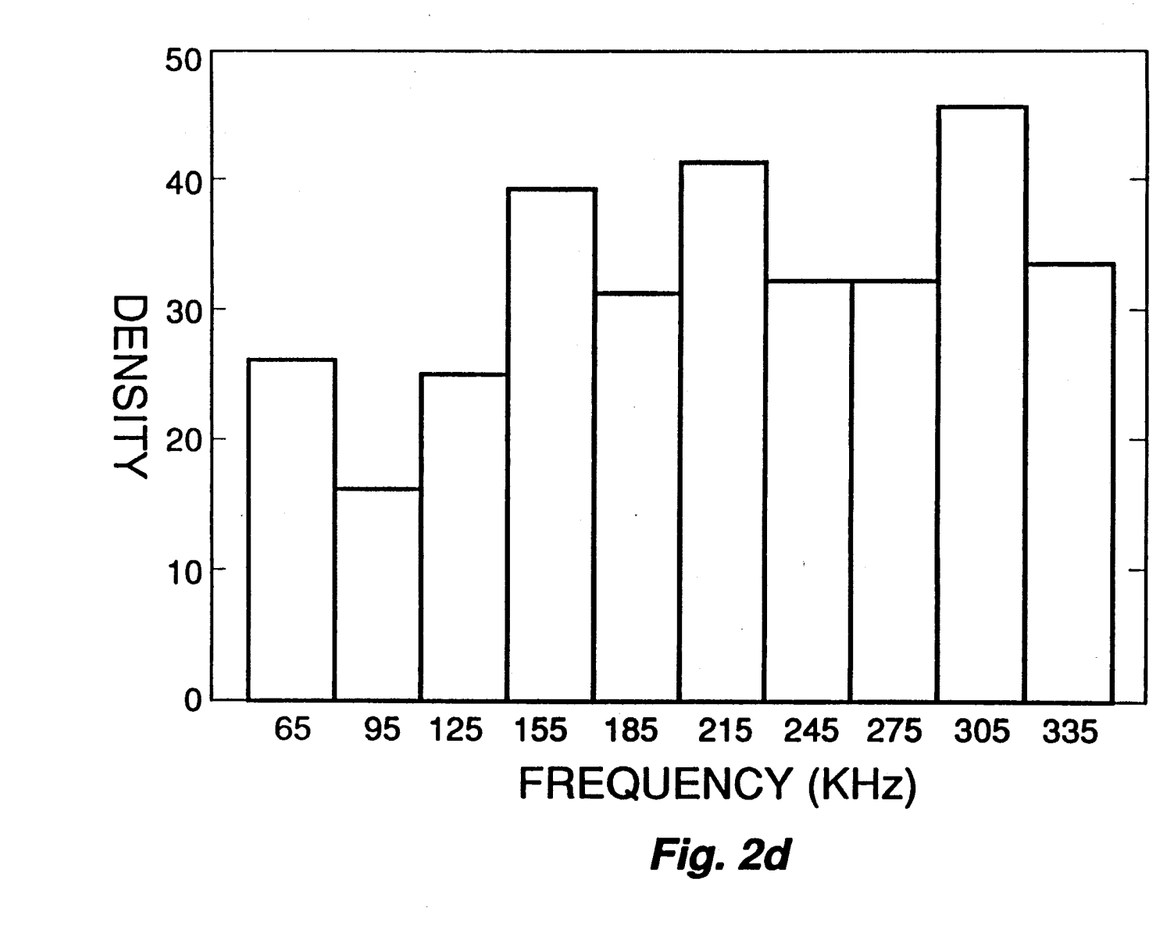
FIG. 2D graphically depicts a histogram characterization calculated from the resonance response shown in FIG. 2A.
Figure 3C:
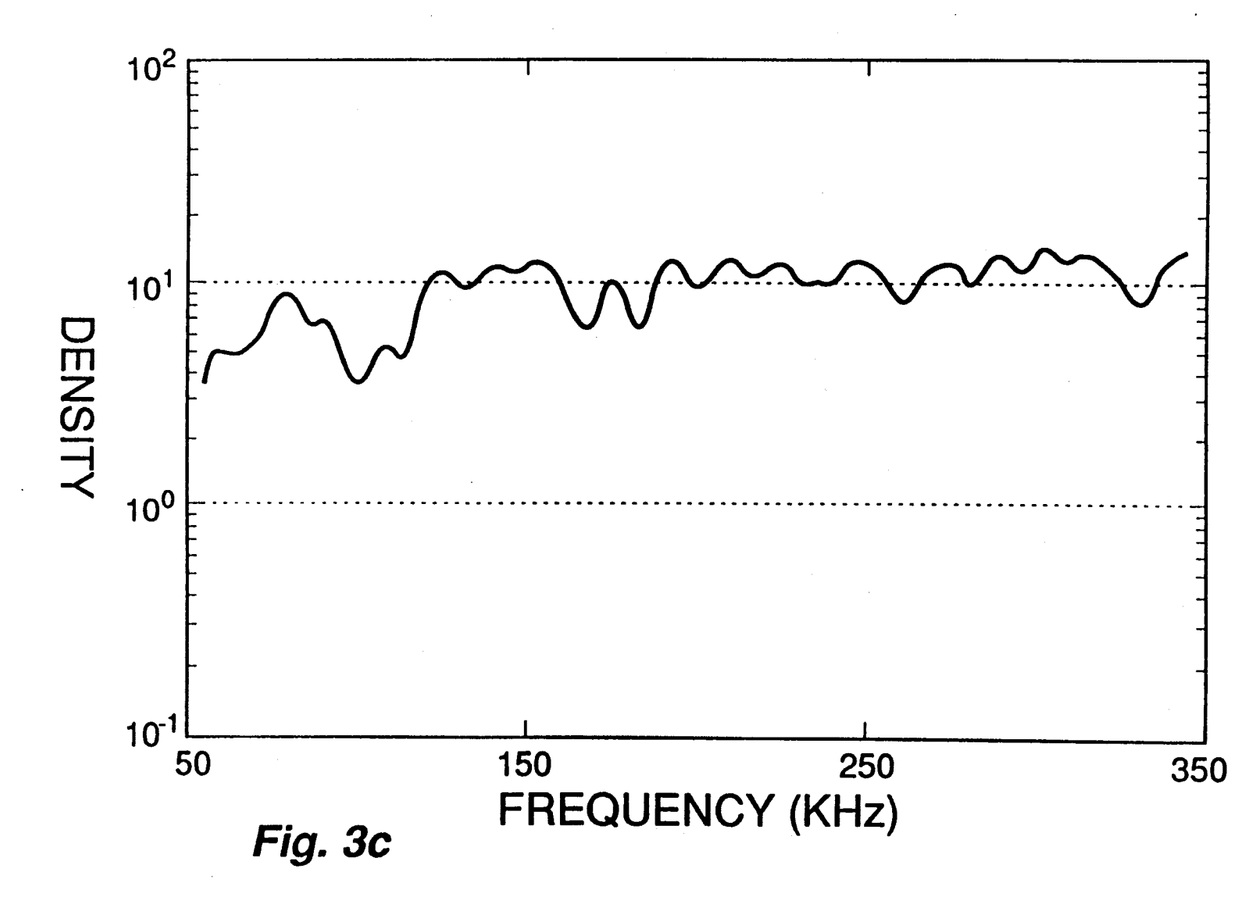
FIG. 3C graphically depicts a resonance characterization calculated from the resonance response shown in FIG. 3A.
Figure 3D:
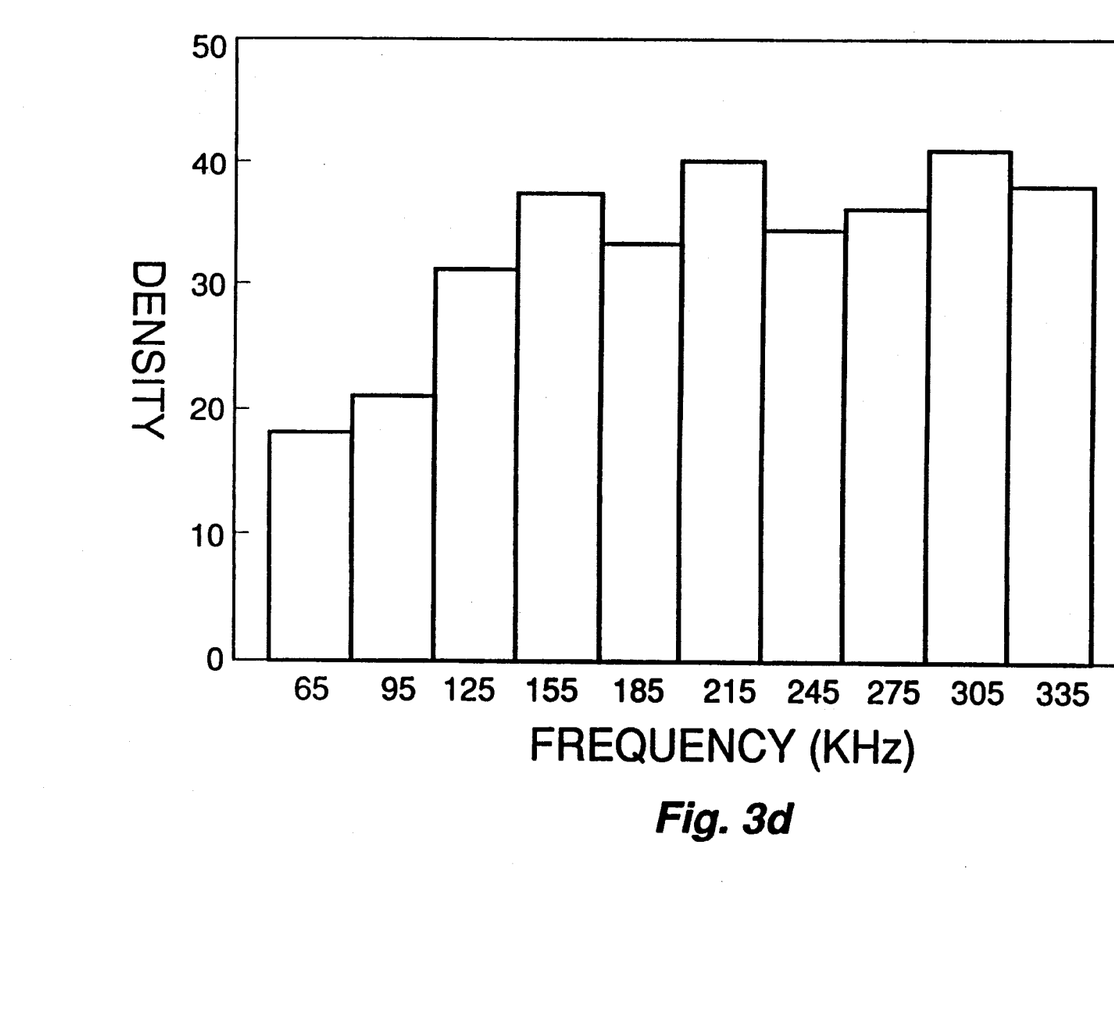
FIG. 3D graphically depicts a resonance characterization calculated from the resonance response shown in FIG. 3A.

As hereinabove discussed, other unique signatures can be formed using Gaussian characterizations and histogram characterizations. FIGS. 2C and 3C illustrate Gaussian signatures for the frequency spectra shown in FIGS. 2A and 3A, respectively. The selected window width Δf was 2 kHz. FIGS. 2D and 3D illustrate histogram signatures using a window width of 30 kHz It is again readily apparent that the sample edge slot relocation of 2 mm produced easily discernible distinctions in both the Gaussian and histogram signatures.

The sensitivity of the above method can also be adjusted by selecting the frequency range over which the resonance density is determined or by adjusting the sweep rate. An increasing sweep rate causes the width of sharp resonances to be increased, obscuring adjacent resonances and increasing the tolerance level of the method. Thus, two objects would be differentiated only when a test object exceeds selected tolerance levels with the reference object. It should be noted that the above technique does not determine the nature or location of the detected anomaly.

While the resonant ultrasound spectroscopy method has obvious application to various manufacturing quality control processes, it also has significant application to arms treaty-verification methods. For example, the method has easily differentiated between full and empty shell casings and may be able to verify the number of warheads inside a rocket or bomb shell.

The foregoing description of embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for characterizing an object by resonant ultrasound spectroscopy, comprising the steps of:
   applying to said object acoustic waves having frequencies swept over a predetermined frequency range;
   detecting a response of said object to said acoustic waves;
   determining the frequency of each resonant response peak in said predetermined frequency range; and
   forming a unique signature of said object from a density distribution of said resonant response frequencies.

2. A method according to claim 1, wherein characterizing said distribution of said resonant response frequencies includes the steps of:
   defining a small response interval;
   stepping said small response interval through said predetermined frequency range at a selected step interval; and
   determining a number of resonant response peaks within said small response interval at each step to form said unique signature of said object.

3. A method according to claim 2, wherein said small response interval and said step interval are selected to obtain a selectivity for said characterization of said object.

4. A method according to claim 1, wherein characterizing said distribution of said resonant response frequencies includes the steps of:
   defining a plurality of frequency steps over said predetermined frequency range; and applying a Gaussian weighted distribution function centered at each frequency step to determine the resonant frequency characterization at said each frequency step.

5. A method according to claim 1, wherein characterizing said distribution of said resonant response frequencies includes the steps of:
   defining a plurality of discrete window intervals over said predetermined frequency range; and
   determining the number of said resonant response frequencies within each said discrete window interval.

6. A method according to claims 1, 2, 4, or 5 further including the steps of:
   forming a first unique signature of a reference object;
   forming a second unique signature of a test object;
   comparing said first and second signature to determine whether said test object is similar to said reference object within a tolerance determined by said step of forming said unique signature from said density distribution of said resonant response frequencies.

* * * * *